(12) United States Patent
Rischel et al.

(10) Patent No.: US 9,186,323 B2
(45) Date of Patent: Nov. 17, 2015

(54) HIGH CONCENTRATION FACTOR VII POLYPEPTIDE FORMULATIONS COMPRISING AN AROMATIC PRESERVATIVE AND AN ANTIOXIDANT

(75) Inventors: Christian Rischel, Copenhagen S (DK); Michael Bech Jensen, Allerød (DK); Anders Dybdal Nielsen, Ballerup (DK)

(73) Assignee: Novo Nordisk Healthcare AG, Zurich (CH)

( * ) Notice: Subject to any disclaimer, the term of this patent is extended or adjusted under 35 U.S.C. 154(b) by 0 days.

(21) Appl. No.: 12/598,518

(22) PCT Filed: Apr. 30, 2008

(86) PCT No.: PCT/EP2008/055348
§ 371 (c)(1),
(2), (4) Date: Dec. 22, 2009

(87) PCT Pub. No.: WO2008/135500
PCT Pub. Date: Nov. 13, 2008

(65) Prior Publication Data
US 2010/0294677 A1   Nov. 25, 2010

Related U.S. Application Data

(60) Provisional application No. 60/927,788, filed on May 4, 2007.

(30) Foreign Application Priority Data

May 2, 2007 (EP) ..................... 07107384

(51) Int. Cl.
| | |
|---|---|
| *A61K 38/00* | (2006.01) |
| *A61K 9/08* | (2006.01) |
| *A61K 9/00* | (2006.01) |
| *A61K 38/48* | (2006.01) |
| *A61K 47/10* | (2006.01) |
| *A61K 47/18* | (2006.01) |
| *C12N 9/64* | (2006.01) |

(52) U.S. Cl.
CPC ................. *A61K 9/08* (2013.01); *A61K 9/0019* (2013.01); *A61K 38/4846* (2013.01); *A61K 47/10* (2013.01); *A61K 47/183* (2013.01); *C12N 9/6437* (2013.01); *C12Y 304/21021* (2013.01)

(58) Field of Classification Search
None
See application file for complete search history.

(56) References Cited

U.S. PATENT DOCUMENTS

| | | | |
|---|---|---|---|
| 4,675,047 A * | 6/1987 | Serban et al. ................. | 504/240 |
| 6,310,183 B1 | 10/2001 | Johannessen et al. | |
| 6,806,063 B2 | 10/2004 | Pedersen et al. | |
| 6,955,834 B2 * | 10/2005 | Rohrbaugh et al. .......... | 427/180 |
| 7,638,165 B2 * | 12/2009 | Jensen Moller .............. | 427/195 |
| 7,732,405 B2 * | 6/2010 | Jensen et al. ................. | 514/14.3 |
| 7,790,852 B2 * | 9/2010 | Hansen et al. ................ | 530/384 |
| 8,318,904 B2 * | 11/2012 | Jensen et al. .................. | 530/384 |
| 2004/0037893 A1 | 2/2004 | Hansen et al. | |
| 2005/0175603 A1 | 8/2005 | Liu et al. | |

FOREIGN PATENT DOCUMENTS

| | | |
|---|---|---|
| CN | 1400910 A | 3/2003 |
| JP | 2004-532798 A | 10/2004 |
| JP | 2005-270110 A | 10/2005 |
| JP | 2005-530683 A | 10/2005 |
| JP | 2006-524195 A | 10/2006 |
| JP | 2007-508235 A | 4/2007 |
| WO | 01/58935 A2 | 8/2001 |
| WO | 02/02764 A2 | 1/2002 |
| WO | 03/055512 A1 | 7/2003 |
| WO | 04/000366 A1 | 12/2003 |
| WO | WO 04/000347 | 12/2003 |
| WO | WO 2004/112828 | 12/2004 |
| WO | WO 2005/002615 | 1/2005 |
| WO | WO 2005/016365 | 2/2005 |
| WO | WO 2005/058283 | 6/2005 |
| WO | 2006/013202 A2 | 2/2006 |
| WO | 2006/042848 A2 | 4/2006 |
| WO | WO 2006/089954 | 8/2006 |
| WO | 2006/114448 A2 | 11/2006 |
| WO | 2007/022784 A2 | 3/2007 |
| WO | 2007/076062 A2 | 7/2007 |
| WO | 2008/025856 A2 | 3/2008 |
| WO | 2008/081024 A1 | 7/2008 |

OTHER PUBLICATIONS

Nema, S. et al., "Excipients and Their Use in Injectable Products", Journal of Pharmaceutical Science & Technology, 1997, vol. 51, No. 4, pp. 166-171.

(Continued)

*Primary Examiner* — Hope Robinson
(74) *Attorney, Agent, or Firm* — Leon Y. Lum (57) ABSTRACT

The present invention relates to pharmaceutical compositions comprising: (i) at least 10 mg/mL of a Factor VII polypeptide; (ii) a buffering agent suitable for keeping pH in the range of from about 5.0 to about 9.0; (iii) at least one aromatic preservative in a concentration of at least 0.1 mg/mL; and (iv) at least one antioxidant in a concentration of at least 0.1 mg/mL; the composition optionally comprising further components, with the proviso that such further components are not Factor VII polypeptide stabilizing agents selected from (a) metal-containing agents, wherein said metal is selected from the group consisting of first transition series metals of oxidation state +II, except zinc; and (b) stabilizing agents comprising a —C(=N—Z1-R1)-NH—Z2-R2 motif.

21 Claims, 2 Drawing Sheets

(56) References Cited

OTHER PUBLICATIONS

Lerche, C.M. et al., "Et studie af microtiterpladers anvendelse i formuleringsscreening af proteiner—med rFVIIa som modelstof", Aug. 2004, English abstract.

Fee et al., Chemical Engineering Science, "PEG-proteins: Reaction engineering and separation issues," 2006, vol. 61, No. 3, pp. 924-939.

\* cited by examiner

HIGH CONCENTRATION FACTOR VII POLYPEPTIDE FORMULATIONS COMPRISING AN AROMATIC PRESERVATIVE AND AN ANTIOXIDANT

CROSS-REFERENCE TO RELATED APPLICATIONS

This application is a 35 U.S.C. §371 national stage application of International Patent Application PCT/EP2008/055348 (published as WO 2008/135500), filed 30 Apr. 2008, which claimed priority of European Patent Application 07107384.5, filed May 2, 2007; this application further claims priority under 35 U.S.C. §119 of U.S. Provisional Application 60/927,788, filed May 4, 2007.

FIELD OF THE INVENTION

The present invention relates to novel ready-to-use Factor VII polypeptide formulations (in the following: liquid aqueous pharmaceutical compositions) comprising a high concentration of a Factor VII polypeptide, a buffering agent, and a combination of at least one aromatic preservative and at least one antioxidant.

BACKGROUND OF THE INVENTION

Factor VII, which is involved in the clotting cascade, has proven to be a useful therapeutic agent to treat a variety of pathological conditions. Accordingly, there is an increasing need for formulations comprising activated Factor VII polypeptides that are pharmaceutically acceptable and exhibit a uniform and predetermined clinical efficacy.

The current commercially available, recombinantly-made Factor VII polypeptide composition NovoSeven® (Novo Nordisk A/S, Denmark), is, e.g., presented as a vial (about 3.0 mL container volume) containing 1.2 mg recombinant human Factor VIIa, 5.84 mg NaCl, 2.94 mg $CaCl_2$, $2H_2O$, 2.64 mg GlyGly, 0.14 mg polysorbate 80, and 60.0 mg mannitol. This product is reconstituted to pH 5.5 by 2.0 mL water for injection (WFI) prior to use, thus yielding a concentration of the Factor VII polypeptide of about 0.6 mg/mL.

For therapeutic applications where administration of larger amounts (e.g. 10-20 mg) of an activated Factor VII polypeptide (e.g. rhFVIIa) is necessary, it is inconvenient to utilize a formulation like the NovoSeven® composition, because a fairly large volume (e.g. 15-30 mL) needs to be administered, typically by injection.

Thus, there is a need for liquid pharmaceutical products comprising an activated Factor VII polypeptide in a relatively high concentration.

Liquid formulations of Factor VII polypeptides are subject to degradation by autolysis. This is particularly acute for high concentration formulations and limits the liquid stability. Liquid formulations of Factor VII polypeptides containing Factor VII inhibitors/stabilizers have previously been described. However, these Factor VII inhibitors/stabilizers must be injected together with the Factor VII polypeptide molecule, and the effect of the Factor VII inhibitors/stabilizers on humans is generally not known.

WO 2005/002615 A1 discloses a liquid, aqueous pharmaceutical composition comprising a Factor VII polypeptide; a buffering agent suitable for keeping pH in the range of from about 5.0 to about 9.0; at least one metal-containing agent, wherein said metal is selected from the group consisting of first transition series metals of oxidation state +II, except zinc; and a non-ionic surfactant. Some ions of this class, e.g. cupper, have known toxicity, which can make some formulations of this type unsuitable for administration to humans.

WO 2005/016365 A1 discloses a liquid, aqueous pharmaceutical composition comprising at least 0.01 mg/mL of a Factor VII polypeptide (i); a buffering agent (ii) suitable for keeping pH in the range of from about 5.0 to about 9.0; and at least one stabilising agent (iii) comprising a —C(=N—$Z^1$—$R^1$)—NH—$Z^2$—$R^2$ motif (e.g. a benzamidine or an arginine). Some compounds of this class, e.g. L-arginine, are known to have a blood pressure lowering effect, which can make some formulations of this type unsuitable for administration to humans.

Liquid formulations are advantageous for injectable pharmaceutical products. If several injection dosages are retrieved from the same vial, a preservative is often a requirement from the regulatory authorities. A number of different compounds have been used as preservatives in injectable products (S, Nema, N. R. Washkuhn and R. J. Brendel: Excipients and their use in injectable products, PDA Journal of Pharmaceutical Science and Technology 51 (4), 166-171).

"Et studie af mikrotiterpladers anvendelse i formuleringsscreening af proteiner-med rFVIIa som modelstof" by Catharina Margrethe Lerche and Charlotte Petersen (Pharmaceutical University of Denmark, 2004) discloses formulations containing 1 mg/mL activated Factor VII and 2 mg/mL metacresol, but no antioxidant. These authors surprisingly found that in the presence of meta-cresol, about 30% of the protein molecules are oxidised after 4 weeks of incubation at 25° C., suggesting that a formulation with preservatives is highly detrimental to the stability of the protein.

SUMMARY OF THE INVENTION

The inventor has discovered that aromatic preservatives in combination with antioxidant inhibit the activity of Factor VII polypeptides (e.g. rFVIIa) and enhance the stability of formulations with high concentrations of Factor VII polypeptides. These compounds are already approved for injection in humans. The invention is based on the hypothesis that the inhibitory action is connected to the aromatic nature of the compounds.

A first aspect of the invention relates to a liquid, aqueous pharmaceutical composition comprising at least 10 mg/mL of a Factor VII polypeptide (i);

a buffering agent (ii) suitable for keeping pH in the range of from about 5.0 to about 9.0;

at least one aromatic preservative (iii) in a concentration of at least 0.1 mg/mL; and at least one antioxidant (iv) in a concentration of at least 0.1 mg/mL;

the composition optionally comprising further components, with the proviso that none of such further components are Factor VII polypeptide stabilizing agents selected from (a) metal-containing agents, wherein said metal is selected from the group consisting of first transition series metals of oxidation state +II, except zinc; and (b) stabilising agent comprising a —C(=N—$Z^1$—$R^1$)—NH—$Z^2$—$R^2$ motif.

A second aspect of the invention relates to a liquid, aqueous pharmaceutical composition as defined herein for use as a medicament.

A third aspect of the invention relates to the use of a liquid, aqueous pharmaceutical composition as defined herein for the preparation of a medicament for treating a Factor VII-responsive syndrome.

A fourth aspect of the invention relates to a method for treating a Factor VII-responsive syndrome, the method comprising administering to a subject in need thereof an effective amount of a liquid, aqueous pharmaceutical composition as defined herein.

A fifth aspect of the invention relates to an air-tight container containing a liquid, aqueous pharmaceutical composition as defined herein, and optionally an inert gas.

A sixth aspect of the invention relates to a kit for the preparation of the composition as defined herein, said kit comprising:

(a) a first container comprising at least the Factor VII polypeptide (i) in freeze-dried form;

(b) a second container comprising an aqueous reconstitution liquid, said liquid at least comprising the buffering agent (ii) and the at least one aromatic preservative (iii).

DETAILED DESCRIPTION OF THE INVENTION

As mentioned above, the present invention resides in the development of a novel stabilised liquid, aqueous pharmaceutical composition comprising a high concentration of a Factor VII polypeptide.

More specifically, the liquid, aqueous pharmaceutical composition comprises
at least 10 mg/mL of a Factor VII polypeptide (i);
a buffering agent (ii) suitable for keeping pH in the range of from about 5.0 to about 9.0;
at least one aromatic preservative (iii) in a concentration of at least 1 mg/mL; and
at least one antioxidant (iv) in a concentration of at least 0.1 mg/mL;
the composition optionally comprising further components, with the proviso that none of such further components are Factor VII polypeptide stabilizing agents selected from (a) metal-containing agents, wherein said metal is selected from the group consisting of first transition series metals of oxidation state +II, except zinc; and (b) stabilising agent comprising a —C(=N—$Z^1$—$R^1$)—NH—$Z^2$—$R^2$ motif.

Factor VII Polypeptide (i)

The biological effect of the pharmaceutical composition is mainly ascribed to the presence of the Factor VII polypeptide, although other active ingredients may be included in combination with the Factor VII polypeptide.

As used herein, the term "Factor VII polypeptide" encompasses wild-type Factor VII (i.e. a polypeptide having the amino acid sequence disclosed in U.S. Pat. No. 4,784,950), variants of Factor VII exhibiting substantially the same or improved biological activity relative to wild-type Factor VII as well as Factor VII derivatives and Factor VII conjugates. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII polypeptide" also encompasses polypeptides, including variants derivatives and conjugates, in which the Factor VIIa biological activity has been substantially modified or somewhat reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively).

For the purposes of the invention, biological activity of Factor VII polypeptides ("Factor VII biological activity") may be quantified by measuring the ability of a preparation to promote blood clotting, cf. Assay 4 described herein. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of a Factor VII polypeptide (e.g., Factor VIIa) to produce activated Factor X (Factor Xa) in a system comprising TF embedded in a lipid membrane and Factor X. (Persson et al., J. Biol. Chem. 272:19919-19924, 1997); (ii) measuring Factor X hydrolysis in an aqueous system ("In Vitro Proteolysis Assay", see Assay 2 below); (iii) measuring the physical binding of a Factor VII polypeptide (e.g., Factor VIIa) to TF using an instrument based on surface plasmon resonance (Persson, FEBS Letts. 413:359-363, 1997); (iv) measuring hydrolysis of a synthetic substrate by a Factor VII polypeptide (e.g., Factor VIIa) ("In Vitro Hydrolysis Assay", see Assay 1 below); or (v) measuring generation of thrombin in a TF-independent in vitro system (see Assay 3 below).

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay (Assay 4), proteolysis assay (Assay 2), or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay (Assay 4), proteolysis assay (Assay 2), or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, US 20040132640, WO2007022512, and US 20070105755 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VII a. The term "PEGylated human Factor VIIa" means human Factor VII a, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of Factor VII variants having increased biological activity compared to wild-type FVIIa include FVII variants as disclosed in WO 01/83725 (Novo Nordisk), WO 02/22776 (Novo Nordisk), WO 02/077218 (Novo Nordisk), WO 03/27147 (Novo Nordisk), WO 03/37932; WO 02/38162 (Scripps Research Institute); and FVIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicolaisen et al., FEBS Letts. 317:245-249, 1993).

Examples of Factor VII polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/

E296V/M298Q-FVII, K316Q/L305V/V158T/K337A/ M298Q-FVII, K316Q/L305V/V158T/E296V/K337A-FVII, K316Q/L305V/V158D/K337A/M298Q-FVII, K316Q/ L305V/V158D/E296V/K337A-FVII, K316Q/L305V/ V158D/E296V/M298Q/K337A-FVII, K316Q/L305V/ V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/ L305V-FVII, F374Y/L305V/K337A-FVII, F374Y/L305V/ V158D-FVII, F374Y/L305V/E296V-FVII, F374Y/L305V/ M298Q-FVII, F374Y/L305V/V158T-FVII, F374Y/L305V/ S314E-FVII, F374Y/K337A/S314E-FVII, F374Y/K337A/ V158T-FVII, F374Y/K337A/M298Q-FVII, F374Y/K337A/ E296V-FVII, F374Y/K337A/V158D-FVII, F374Y/V158D/ S314E-FVII, F374Y/V158D/M298Q-FVII, F374Y/V158D/ E296V-FVII, F374Y/V158T/S314E-FVII, F374Y/V158T/ M298Q-FVII, F374Y/V158T/E296V-FVII, F374Y/E296V/ S314E-FVII, F374Y/S314E/M298Q-FVII, F374Y/E296V/ M298Q-FVII, F374Y/L305V/K337A/V158D-FVII, F374Y/ L305V/K337A/E296V-FVII, F374Y/L305V/K337A/ M298Q-FVII, F374Y/L305V/K337A/V158T-FVII, F374Y/ L305V/K337A/S314E-FVII, F374Y/L305V/V158D/ E296V-FVII, F374Y/L305V/V158D/M298Q-FVII, F374Y/ L305V/V158D/S314E-FVII, F374Y/L305V/E296V/ M298Q-FVII, F374Y/L305V/E296V/V158T-FVII, F374Y/ L305V/E296V/S314E-FVII, F374Y/L305V/M298Q/ V158T-FVII, F374Y/L305V/M298Q/S314E-FVII, F374Y/ L305V/V158T/S314E-FVII, F374Y/K337A/S314E/V158T-FVII, F374Y/K337A/S314E/M298Q-FVII, F374Y/K337A/ S314E/E296V-FVII, F374Y/K337A/S314E/V158D-FVII, F374Y/K337A/V158T/M298Q-FVII, F374Y/K337A/ V158T/E296V-FVII, F374Y/K337A/M298Q/E296V-FVII, F374Y/K337A/M298Q/V158D-FVII, F374Y/K337A/ E296V/V158D-FVII, F374Y/V158D/S314E/M298Q-FVII, F374Y/V158D/S314E/E296V-FVII, F374Y/V158D/ M298Q/E296V-FVII, F374Y/V158T/S314E/E296V-FVII, F374Y/V158T/S314E/M298Q-FVII, F374Y/V158T/ M298Q/E296V-FVII, F374Y/E296V/S314E/M298Q-FVII, F374Y/L305V/M298Q/K337A/S314E-FVII, F374Y/ L305V/E296V/K337A/S314E-FVII, F374Y/E296V/ M298Q/K337A/S314E-FVII, F374Y/L305V/E296V/ M298Q/K337A-FVII, F374Y/L305V/E296V/M298Q/ S314E-FVII, F374Y/V158D/E296V/M298Q/K337A-FVII, F374Y/V158D/E296V/M298Q/S314E-FVII, F374Y/ L305V/V158D/K337A/S314E-FVII, F374Y/V158D/ M298Q/K337A/S314E-FVII, F374Y/V158D/E296V/ K337A/S314E-FVII, F374Y/L305V/V158D/E296V/ M298Q-FVII, F374Y/L305V/V158D/M298Q/K337A-FVII, F374Y/L305V/V158D/E296V/K337A-FVII, F374Y/ L305V/V158D/M298Q/S314E-FVII, F374Y/L305V/ V158D/E296V/S314E-FVII, F374Y/V158T/E296V/ M298Q/K337A-FVII, F374Y/V158T/E296V/M298Q/ S314E-FVII, F374Y/L305V/V158T/K337A/S314E-FVII, F374Y/V158T/M298Q/K337A/S314E-FVII, F374Y/ V158T/E296V/K337A/S314E-FVII, F374Y/L305V/ V158T/E296V/M298Q-FVII, F374Y/L305V/V158T/ M298Q/K337A-FVII, F374Y/L305V/V158T/E296V/ K337A-FVII, F374Y/L305V/V158T/M298Q/S314E-FVII, F374Y/L305V/V158T/E296V/S314E-FVII, F374Y/E296V/ M298Q/K337A/V158T/S314E-FVII, F374Y/V158D/ E296V/M298Q/K337A/S314E-FVII, F374Y/L305V/ V158D/E296V/M298Q/S314E-FVII, F374Y/L305V/ E296V/M298Q/K337A/V158T-FVII, F374Y/L305V/ E296V/M298Q/K337A/V158T-FVII, F374Y/L305V/ E296V/K337A/V158T/S314E-FVII, F374Y/L305V/ M298Q/K337A/V158T/S314E-FVII, F374Y/L305V/ V158D/E296V/M298Q/K337A-FVII, F374Y/L305V/ V158D/E296V/M298Q/K337A/S314E-FVII, F374Y/L305V/ V158D/M298Q/K337A/S314E-FVII, F374Y/L305V/ E296V/M298Q/K337A/V158T/S314E-FVII, F374Y/ L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/ V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L3051, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

In some embodiments, the Factor VII polypeptide is human Factor VIIa (hFVIIa), preferably recombinantly made human Factor VIIa (rhVIIa).

In other embodiments, the Factor VII polypeptide is a Factor VII sequence variant.

In some embodiments, the Factor VII polypeptide has a glycosylation different from wild-type human Factor VII.

In some embodiments, the Factor VII polypeptide is a pegylated FVII derivative, preferably a glycopegylated FVII derivative.

In the currently most interesting embodiment, the protein is a Factor VII polypeptide in activated form.

In various embodiments, e.g. those where the Factor VII polypeptide is a Factor VII sequence variant, the ratio between the activity of the Factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" (Assay 2) as described in the present specification.

In some embodiments, the Factor VII polypeptides are Factor VII variants, wherein the ratio between the activity of said Factor VII polypeptide and the activity of native human Factor VIIa (wild-type FVIIa) is at least about 1.25 when tested in the "In Vitro Hydrolysis Assay" (see Assay 1 below); in other embodiments, the ratio is at least about 2.0; in further embodiments, the ratio is at least about 4.0.

In a pharmaceutical composition, it is often desirable that the concentration of the active ingredient is such that the application of a unit dose does not cause unnecessary discomfort to the patient. Thus, a unit dose of more than about 2-10 mL is often undesirable. For the purpose of the present invention, the concentration of the Factor VII polypeptide is therefore fairly high, i.e. at least 10 mg/mL. In different embodiments, the Factor VII polypeptide is present in a concentration of 10-90 mg/mL; 12-80 mg/mL; 16-80 mg/mL; 22-70 mg/mL; 22-60 mg/mL; 22-50 mg/mL; or 25-50 mg/mL.

Factor VIIa concentration is conveniently expressed as mg/mL or as IU/mL, with 1 mg usually representing 43,000-56,000 IU or more.

Buffering Agent (ii)

In order to render the liquid, aqueous pharmaceutical composition useful for direct parenteral administration to a mammal such as a human, it is normally required that the pH value of the composition is held within reasonable limits, such as from about 5.0 to about 9.0. To ensure a suitable pH value under the conditions given, the pharmaceutical composition also comprises a buffering agent (ii) suitable for keeping pH in the range of from about 5.0 to about 9.0.

The term "buffering agent" encompasses those agents or combinations of agents which maintain the solution pH in an acceptable range from about 5.0 to about 9.0.

In one embodiment, the buffering agent (ii) is at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium or calcium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

The concentration of the buffering agent is chosen so as to maintain the preferred pH of the solution. In various embodiments, the concentration of the buffering agent is 1-100 mM; 1-50 mM; 1-25 mM; or 2-20 mM.

In one embodiment, the pH of the composition is kept from about 5.0 to about 8.0; such as from about 5.0 to about 7.5; from about 5.0 and about 7.0; from about 5.0 to about 6.5, from about 5.0 to about 6.0, from about 5.5 to about 7.0; from about 5.5 to about 6.5, from about 6.0 to about 7.0, from about 6.4 to about 6.6, or from about 5.2 to about 5.7.

Aromatic Preservative(s) (iii)

The pharmaceutical composition further comprises at least one aromatic preservative (iii) in a concentration of at least 0.1 mg/mL.

Preservatives are typically included in the composition to retard microbial growth (i.e. the aromatic preservative has bacteriostatic/bacteriocidal effects) and thereby allow "multiple dose" packaging of the Factor VII polypeptides. However, it has been found that the aromatic preservative(s), in combination with the antioxidant(s), also have a very pronounced effect on the stability of Factor VII polypeptides in aqueous solution, in particular at fairly high concentrations.

In the following, the term "aromatic" refers to chemical compounds containing in their structure a 6-membered unsaturated ring of carbon atoms (i.e. a benzene ring).

Examples of aromatic preservatives include phenol, benzyl alcohol, orto-cresol, meta-cresol, para-cresol, chloro-cresol, methyl paraben, propyl paraben, benzalkonium chloride, and benzethonium chloride.

The at least one aromatic preservative (iii) is normally included at a concentration of 0.1-20 mg/mL depending on the pH range and type of aromatic preservative. For example, typical concentrations are 1-4 mg/mL meta-cresol, or 1-6 mg/mL phenol, or 5-20 mg/mL benzyl alcohol, or 1-3 mg/mL chlorocresol.

Antioxidant(s) (iv)

As mentioned above, the stability of the Factor VII polypeptide in the aqueous composition is ascribed the combination of the aromatic preservative(s) (iii) and the antioxidant(s) (iv). The at least one antioxidant is present in concentration of at least 0.1 mg/mL.

In different embodiments, the at least one antioxidant (iv) is selected from the group consisting of L-methionine, D-methionine, methionine analogues, methionine-containing peptides, methionine-homologues, ascorbic acid, cysteine, homocysteine, gluthatione, cystine, and cysstathionine. In a preferred embodiment, the antioxidant is L-methionine.

The concentration of the at least one antioxidant is typically 0.1-5.0 mg/mL, such as 0.1-4.0 mg/mL, 0.1-3.0 mg/mL, 0.1-2.0 mg/mL, or 0.5-2.0 mg/mL.

The inventors have discovered that oxidation of activated Factor VII in fact proceeds very slowly in the simultaneous presence of an aromatic preservative and an antioxidant (e.g. 0.5 mg/mL methionine).

Further Components

It should be understood that combination of the presence of the preservative(s) and the antioxidant(s) eliminates the need for a stabilising agent of the types (a) and (b) above, and in more preferred embodiment even eliminates the need for further Factor VII polypeptide stabilising agents. Hence, in a preferred embodiment, none of said further components of the composition are Factor VII polypeptide stabilizing agents.

With respect to the stabilising agents of type (a), these are described and defined in WO 2005/002615.

With respect to the stabilising agents of type (b), these are described and defined (in general and explicitly with respect to the detailed meaning of the substituents $Z^1$, $Z^2$, $R^1$ and $R^2$) in WO 2005/016365. For convenience it should although be mentioned that $Z^1$ and $Z^2$ independently are selected from the group consisting of —O—, —S—, $NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or $Z^2$ and $R^2$ are as defined above and —C=N—$Z^1$—$R^1$ forms part of a heterocyclic ring, or $Z^1$ and $R^1$ are as defined above and —C—NH—$Z^2$—$R^2$ forms part of a heterocyclic ring, or —C(=N—$Z^1$—$R^1$)—NH—$Z^2$—$R^2$ forms a heterocyclic ring wherein $Z^1$—$R^1$—$R^2$—$Z^2$ is a biradical.

This being said, the liquid, aqueous pharmaceutical composition may, in addition to the mandatory components, comprise additional components beneficial for the preparation, formulation, or administration of the composition.

In some embodiments, the composition further comprises a tonicity modifying agent (v).

As used herein, the term "tonicity modifying agent" includes agents which contribute to the osmolality of the solution. The tonicity modifying agent (v) includes at least one agent selected from the group consisting of neutral salts, amino acids, peptides of 2-5 amino acid residues, monosaccharides, disaccharides, polysaccharides, and sugar alcohols. In some embodiments, the composition comprises two or more of such agents in combination.

By "neutral salt" is meant a salt that is neither an acid nor a base when dissolved in an aqueous solution.

In one embodiment, at least one tonicity modifying agent (v) is a neutral salt selected from the groups consisting of sodium salts, potassium salts, calcium salts, and magnesium salts, such as sodium chloride, potassium chloride, calcium chloride, calcium acetate, calcium gluconate, calcium laevulate, magnesium chloride, magnesium acetate, magnesium gluconate, and magnesium laevulate.

In a further embodiment, the tonicity modifying agent (v) includes sodium chloride in combination with at least one selected from the groups consisting of calcium chloride, calcium acetate, magnesium chloride and magnesium acetate.

In a still further embodiment, the tonicity modifying agent (v) is at least one selected from the group consisting of sodium chloride, calcium chloride, sucrose, glucose, and mannitol.

In different embodiments, the tonicity modifying agent (v) is present in a concentration of at least 1 mM, at least 5 mM, at least 10 mM, at least 20 mM, at least 50 mM, at least 100 mM, at least 200 mM, at least 400 mM, at least 800 mM, at least 1000 mM, at least 1200 mM, at least 1500 mM, at least 1800 mM, at least 2000 mM, or at least 2200 mM.

In one series of embodiments, the tonicity modifying agent (v) is present in a concentration of 5-2200 mM, such as 25-2200 mM, 50-2200 mM, 100-2200 mM, 200-2200 mM, 400-2200 mM, 600-2200 mM, 800-2200 mM, 1000-2200 mM, 1200-2200 mM, 1400-2200 mM, 1600-2200 mM, 1800-2200 mM, or 2000-2200 mM; 5-1800 mM, 25-1800 mM, 50-1800 mM, 100-1800 mM, 200-1800 mM, 400-1800 mM, 600-1800 mM, 800-1800 mM, 1000-1800 mM, 1200-1800 mM, 1400-1800 mM, 1600-1800 mM; 5-1500 mM, 25-1400 mM, 50-1500 mM, 100-1500 mM, 200-1500 mM, 400-1500 mM, 600-1500 mM, 800-1500 mM, 1000-1500 mM, 1200-1500 mM; 5-1200 mM, 25-1200 mM, 50-1200 mM, 100-1200 mM, 200-1200 mM, 400-1200 mM, 600-1200 mM, or 800-1200 mM.

In a preferred embodiment of the invention, at least one tonicity modifying agent (v) is an ionic strength modifying agent (v/a).

As used herein, the term "ionic strength modifying agent" includes agents which contribute to the ionic strength of the solution. The agents include, but are not limited to, neutral salts, amino acids, peptides of 2 to 5 amino acid residues. In some embodiments, the composition comprises two or more of such agents in combination.

Preferred examples of ionic strength modifying agents (v/a) are neutral salts such as sodium chloride, potassium chloride, calcium chloride and magnesium chloride. A preferred agent (v/a) is sodium chloride.

The term "ionic strength" is the ionic strength of the solution (μ) which is defined by the equation: $\mu = \frac{1}{2}\Sigma([i](Z_i^2))$, where μ is the ionic strength, [i] is the millimolar concentration of an ion, and $Z_i$, is the charge (+ or −) of that ion "(see, e.g., Solomon, Journal of Chemical Education, 78(12):1691-92, 2001; James Fritz and George Schenk: Quantitative Analytical Chemistry, 1979).

In different embodiments of the invention, the ionic strength of the composition is at least 50, such as at least 75, at least 100, at least 150, at least 200, at least 250, at least 400, at least 500, at least 650, at least 800, at least 1000, at least 1200, at least 1600, at least 2000, at least 2400, at least 2800, or at least 3200.

In some specific embodiments, the total concentration of the tonicity modifying agent (v) and the ionic strength modifying agent (v/a) is in the range of 1-500 mM, such as 1-300 mM, or 10-200 mM, or 20-150 mM, depending on the effect any other ingredients may have on the tonicity and ionic strength.

In one embodiment, the composition is isotonic; in another, it is hypertonic.

The term "isotonic" means "isotonic with serum", i.e. at about 300±50 milliosmol/kg. The tonicity is meant to be a measure of osmolality of the solution prior to administration.

The term "hypertonic" is meant to designate levels of osmolality above the physiological level of serum, such as levels above 300±50 milliosmol/kg.

Also, a particular embodiment of the present invention relates to the combination of the aromatic preservative(s) (iii) and antioxidant(s) (iv) with a fairly high concentration of an ionic strength modifying agent (v/a) selected from the group consisting of sodium salts, calcium salts and magnesium salts. In this embodiment, the ionic strength modifying agent (v/a), i.e. the sodium salt, calcium salt and/or magnesium salt, is present in a concentration of 15-1000 mM, such as 25-1000 mM, 50-1000 mM, 100-1000 mM, 200-1000 mM, 300-1000 mM, 400-1000 mM, 500-1000 mM, 600-1000 mM, 700-1000 mM; 15-800 mM, 25-800 mM, 50-800 mM, 100-800 mM, 200-800 mM, 300-800 mM, 400-800 mM, 500-800 mM; 15-600 mM, 25-600 mM, 50-600 mM, 100-600 mM, 200-600 mM, 300-600 mM; 15-400 mM, 25-400 mM, 50-400 mM, or 100-400 mM.

Within these embodiments, sodium salt may be sodium chloride, the calcium salt may be selected from the group consisting of calcium chloride, calcium acetate, calcium gluconate, and calcium laevulate, and the magnesium salt may be selected from the group consisting of magnesium chloride, magnesium acetate, magnesium gluconate, magnesium laevulate, and magnesium salts of strong acids. In a more specific embodiment, a calcium salt and/or a magnesium salt is/are used in combination with sodium chloride.

In one currently preferred embodiment, the composition comprises one or more ionic strength modifying agents selected from the group consisting of calcium ($Ca^{2+}$) salts and magnesium ($Mg^{3+}$) salts, e.g. one or more salts selected from the group consisting of calcium chloride, calcium acetate, calcium gluconate, calcium laevulate, magnesium chloride, magnesium acetate, magnesium sulphate, magnesium gluconate, magnesium laevulate, magnesium salts of strong acids. In one embodiment hereof, the concentration of the calcium ($Ca^{2+}$) and/or magnesium ($Mg^{3+}$) salt(s) is at least 2 mM, such as at least 5 mM or about 10 mM. In a particular embodiment, the composition comprises $Ca^{2+}$ in a concentration of at least 2 mM.

In further embodiment, which may be combined with the foregoing, the pharmaceutical composition may also include a non-ionic surfactant (vi). Surfactants (also known as detergents) generally include those agents which protect the protein from air/solution interface induced stresses and solution/surface induced stresses (e.g. resulting in protein aggregation).

Typical types of non-ionic surfactants are polysorbates, poloxamers, polyoxyethylene alkyl ethers, polyethylene/polypropylene block co-polymers, polyethyleneglycol (PEG), polyxyethylene stearates, and polyoxyethylene castor oils.

Illustrative examples of non-ionic surfactants are TWEEN®, polysorbate 20, polysorbate 80, Brij-35 (polyoxyethylene dodecyl ether), poloxamer 188, poloxamer 407, PEG8000, PLURONIC® polyols, polyoxy-23-lauryl ether, Myrj 49, and Cremophor A, in particular poloxamer 188.

In one embodiment, the non-ionic surfactant is present in an amount of 1.005-2.0% by weight.

Preferred Embodiment

The present inventors have presently identified the following embodiment as particularly advantageous, namely the liquid, aqueous pharmaceutical composition as defined herein, which comprises:

10-90 mg/mL of a Factor VII polypeptide (i);

a buffering agent (ii) suitable for keeping pH in the range of from about 5.0 to about 9.0;

at least one aromatic preservative (iii) in a concentration of 0.1-20 mg/mL; and at least one antioxidant (iv) in a concentration of 0.1-5.0 mg/mL.

Stability

The compositions according to the present invention are useful as stable ready-to-use compositions of Factor VII polypeptides. The compositions should typically be stable for at least six months, and preferably up to 36 months, when stored at temperatures ranging from 2° C. to 8° C.

The term "Stable" is intended to denote that (i) after storage for 6 months at 2° C. to 8° C. the composition retains at least 50% of its initial biological activity as measured by a one-stage clot assay (Assay 4), or (ii) after storage for 6 months at 2° C. to 8° C., the content of heavy chain degradation products is at the most 40% (w/w) assuming that the initial sample comprises no heavy chain degradation products (i.e. only the Factor VII polypeptide is entered into the calculation of the percentage). Preferably, the composition retains at least 70%, such as at least 80%, or at least 85%, or at least 90%, or at least 95%, of its initial activity after storage for 6 months at 2 to 8° C. Also preferably, the content of heavy chain degradation products in the composition is at the most 30% (w/w), at the most 25% (w/w), at the most 20% (w/w), at the most 15% (w/w), at the most 10% (w/w), at the most 5% (w/w), or at the most 3% (w/w).

Preferably, the stable composition retains at least 70%, such as at least 80%, or at least 85%, or at least 90%, or at least 95%, of its initial activity after storage for 6 months at 2 to 8° C.

Preferably, in various embodiments the content of heavy chain degradation products in stable compositions is at the most 30% (w/w), at the most 25% (w/w), at the most 20% (w/w), at the most 15% (w/w), at the most 10% (w/w), at the most 5% (w/w), or at the most 3% (w/w).

Methods of Use

As will be understood, the liquid, aqueous pharmaceutical compositions defined herein can be used in the field of medicine. Thus, the present invention in particular provides the liquid, aqueous pharmaceutical compositions defined herein for use as a medicament, more particular for use as a medicament for treating a Factor VII-responsive syndrome.

Consequently, the present invention also provides the use of the liquid, aqueous pharmaceutical composition as defined herein for the preparation of a medicament for treating a Factor VII-responsive syndrome, as well as a method for treating a Factor VII-responsive syndrome, the method comprising administering to a subject in need thereof an effective amount of the liquid, aqueous pharmaceutical composition as defined herein.

The preparations of the present invention may be used to treat any Factor VII-responsive syndrome, such as, e.g., bleeding disorders, including those caused by clotting Factor deficiencies (e.g., haemophilia A, haemophilia B, coagulation Factor XI deficiency, coagulation Factor VII deficiency); by thrombocytopenia or von Willebrand's disease, or by acquisition of clotting Factor inhibitors, and intracerebral haemorrhage, or excessive bleeding from any cause (e.g. trauma, surgery). The preparations may also be administered to patients in association with surgery or other trauma or to patients receiving anticoagulant therapy.

The term "effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

The term "treatment" is defined as the management and care of a subject, e.g. a mammal, in particular a human, for the purpose of combating the disease, condition, or disorder and includes the administration of a Factor VII polypeptide to prevent the onset of the symptoms or complications, or alleviating the symptoms or complications, or eliminating the disease, condition, or disorder. Pharmaceutical compositions according to the present invention containing a Factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

In important embodiments, the pharmaceutical composition is adapted to subcutaneous, intramuscular or intravenous injection according to methods known in the art.

Air-Tight Container

Thus, the present invention also provides an air-tight container (e.g. a vial or a cartridge (such as a cartridge for a pen applicator)) containing a liquid, aqueous pharmaceutical composition as defined herein, and optionally an inert gas.

The inert gas may be selected from the groups consisting of nitrogen, argon, etc. The container (e.g. vial or cartridge) is typically made of glass or plastic, in particular glass, optionally closed by a rubber septum or other closure means allowing for penetration with preservation of the integrity of the pharmaceutical composition. In a further embodiment, the container is a vial or cartridge enclosed in a sealed bag, e.g. a sealed plastic bag, such as a laminated (e.g. metal (such as aluminium) laminated plastic bag).

A Kit Comprising a Freeze-Dried Factor Vii Polypeptide

The above defined liquid, aqueous pharmaceutical composition is mainly intended for direct use, typically for parenteral administration, e.g. by injection. It is, however, also envisaged that the this liquid, aqueous pharmaceutical composition may be prepared from the corresponding freeze-dried formulation some time before the actual parenteral use by the practitioner or the end-user, e.g. 1-24 hours before use, or even some weeks, e.g. 2-4 weeks before use, for example in the form of a multiple dose batch. In such instances it is convenient for the practitioner or end-user to receive the Factor VII polypeptide in freeze-dried form together the suitable amount of aqueous reconstitution liquid.

Hence, a further aspect of the present invention relates to kit for the preparation of the composition as defined herein, said kit comprising:

(a) a first container comprising at least the Factor VII polypeptide (i) in freeze-dried form;

(b) a second container comprising an aqueous reconstitution liquid, said liquid at least comprising the buffering agent (ii) and the at least one aromatic preservative (iii).

Conveniently, the second container also comprises the antioxidant (iv).

In some embodiments, the first container and the second container may be arranged as separate compartment of a device, e.g. an ampoule for a syringe device, e.g. a pen.

Experimentals

General Methods

Percentages are (weight/weight) both when referring to solids dissolved in solution and liquids mixed into solutions. For example, for Poloxamer 188, it is the weight of 100% stock/weight of solution.

Assays Suitable for Determining Biological Activity of Factor VII Polypeptides

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

1st Generation Clot Assay

The activity of the Factor VII polypeptides may be measured using a one-stage clot assay essentially as described in WO 92/15686 or U.S. Pat. No. 5,997,864. Briefly, the sample to be tested is diluted in 50 mM Tris (pH 7.5), 0.1% BSA and 100 µL is incubated with 100 µL of Factor VII deficient plasma and 200 µL of thromboplastin C containing 10 mM Ca2+. Clotting times are measured and compared to a standard curve using a reference standard or a pool of citrated normal human plasma in serial dilution.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a Spectra MaX™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=(A405 nm Factor VII polypeptide)/(A405 nm Factor VIIa wild-type).

Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

This assay can also be used to probe the activity of Factor VII under different buffer conditions.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 µL 50 mM HEPES, pH 7.4, containing 0.1 M NaCl, 5 mM $CaCl_2$ and 1 mg/mL bovine serum albumin, are incubated for 15 min. Factor X cleavage is then stopped by the addition of 50 µL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a Spectra Max™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=(A405 nm Factor VII polypeptide)/(A405 nm Factor VIIa wild-type).

Based thereon, a Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

Thrombin Generation Assay (Assay 3)

The ability of a Factor VII polypeptides to generate thrombin can be measured in an assay (Assay 3) comprising all relevant coagulation Factors and inhibitors at physiological concentrations (minus Factor VIII when mimicking hemophilia A conditions) and activated platelets (as described on p. 543 in Monroe et al. (1997) Brit. J. Haematol. 99, 542-547 which is hereby incorporated as reference).

One-Stage Coagulation Assay (Clot Assay) (Assay 4)

Factor VII polypeptides may also be assayed for specific activities ("clot activity") by using a one-stage coagulation assay (Assay 4). For this purpose, the sample to be tested is diluted in 50 mM PIPES-buffer (pH 7.2), 1% BSA and 40 µl is incubated with 40 µl of Factor VII deficient plasma and 80 µl of human recombinant tissue factor containing 10 mM $Ca^{2+}$ and synthetic phospholipids. Coagulation times (clotting times) are measured and compared to a standard curve using a reference standard in a parallel line assay.

Heavy Chain Degradation Assay

For the purpose of determining the content of heavy chain degradation products, a reverse phase HPLC was run on a proprietary 4.5×250 mm butyl-bonded silica column with a particle size of 5 µm and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13) % B in 30 minutes. X was adjusted so that FVIIa elutes with a retention time of approximately 26 minutes. Flow rate: 1.0 mL/min. Detection: 214 nm. Load: 25 µg FVIIa. The initial content of heavy chain degradation products is subtracted from the measured content of heavy chain degradation product, i.e. the initial content of heavy chain degradation products is set to 0%. The content of heavy chain degradation products at the time x is then calculated as:

$$\% = (HCDP(x) - HCDP(0))/(HCDP(x) - HCDP(0) + FVII(x)) \times 100\%$$

$$= (HCDP(x) - HCDP(0))/(FVII(0)) \times 100\%$$

wherein HCDP(x) is the measured content of heavy chain degradation products at the time x, HCDP(0) is the measured initial content of heavy chain degradation products, and FVII(x) is the content of the intact Factor VII polypeptide at the time x.

Determination of Oxidised Products by Reverse Phase HPLC

HPLC Column: 4.5×250 mm column packed with butyl-bonded silica with a particle size of 5 µm and pore size 300 Å.

Column temperature: 70° C. Eluent A: water 99.9% v/v and trifluoracetic acid 0.1% v/v. Eluent B: acetonitrile 80% v/v, trifluoracetic acid 0.09% v/v and water 19.91% v/v. The column was eluted with a linear gradient from X % B to (X+13) % B in 30 minutes. Flow rate: 1.0 mL/min. Detection: 214 nm.

The oxidised forms are methionine sulfoxides of Factor VII polypeptides. For example the two main derivatives of FVII are Met(O)298 FVII and Met(O)306 FVII.

The content of oxidised forms is expressed as the percentage of the initial amount of Factor VII polypeptide in the composition upon preparation that is recovered as oxidised forms of Factor VII polypeptide.

Preparation and Purification of Factor VII Polypeptides

Human purified Factor VIIa suitable for use in the present invention is preferably made by DNA recombinant technology, e.g. as described by Hagen et al., Proc. Natl. Acad. Sci. USA 83: 2412-2416, 1986, or as described in European Patent No. 0 200 421 (ZymoGenetics, Inc.).

Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation Factors. An even further purified Factor VII preparation may be obtained by including an additional gel filtration as the final purification step. Factor VII is then converted into activated Factor VIIa by known means, e.g. by several different plasma proteins, such as Factor XIIa, IX a or Xa. Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like, or by autoactivation in solution.

Factor VII polypeptides including variants may be produced by modification of wild-type Factor VII or by recombinant technology. Factor VII polypeptides with altered amino acid sequence when compared to wild-type Factor VII may be produced by modifying the nucleic acid sequence encoding wild-type Factor VII either by altering the amino acid codons or by removal of some of the amino acid codons in the nucleic acid encoding the natural Factor VII by known means, e.g. by site-specific mutagenesis.

It will be apparent to those skilled in the art that substitutions can be made outside the regions critical to the function of the Factor VIIa molecule and still result in an active polypeptide. Amino acid residues essential to the activity of the Factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super-coiled, double-stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemi-methylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than 10% by weight, more preferably less than 5% and most preferably less than 1%, of non-Factor VII polypeptides derived from the host cell. Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution. The resulting activated Factor VII polypeptide may then be formulated and administered as described in the present application.

The following examples illustrate practice of the invention. These examples are included for illustrative purposes only and are not intended in any way to limit the scope of the invention claimed.

WORKING EXAMPLES

Example 1

Figure 1:
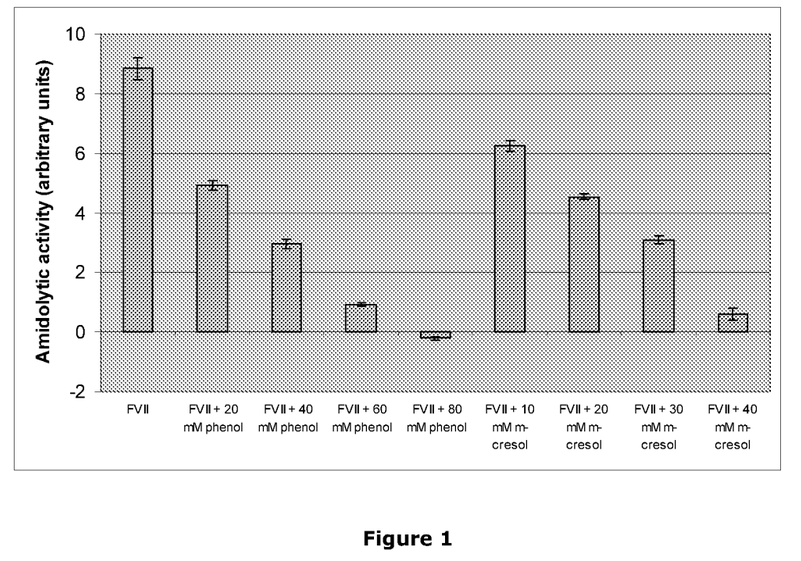
FIG. 1. Amidolytic activity of rFVIIa in the presence of selected aromatic preservatives (phenol and m-cresol).

The amidolytic activity of activated Factor VII was measured by degradation of D-ILE-PRO-ARG-P-NITROANIL-IDE as described above, under the following conditions: 3 μM activated Factor VII 50 mM imidazole, pH 6.5, 20 mM $CaCl_2$, 50 mM NaCl, 0.5 mg/mL bovine serum albumin, 1 mM S-2288. The activity was measured at a number of different concentrations of meta-cresol and phenol. All experiments were performed in duplicate. FIG. 1 shows the amidolytic activity at different preservative concentrations, in arbitrary units. Surprisingly, it is seen that the activity decreases with increasing preservative concentration.

Example 2

Figure 2:
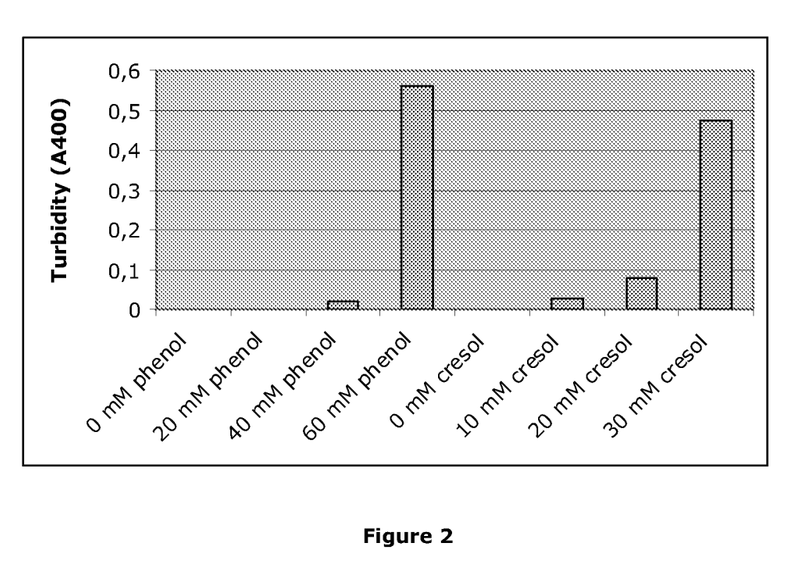
FIG. 2. Turbidity of 15 mg/mL rFVIIa in the presence of increasing concentration of selected preservatives (phenol and m-cresol).

Activated Factor VII was mixed with different concentrations of meta-cresol or phenol under the following conditions: 15 mg/mL Activated Factor VII, 10 mM histidine, pH 6.0, 20 mM $CaCl_2$, 8% sucrose. Samples with total volumes of 100 µl were dispensed into a quartz microtiter plate (Hellma) and the turbidity was assessed by measuring the absorption at 400 nm in a plate reader. Turbidity is a sign of precipitation in the sample. It is seen that at the highest preservative concentrations investigated, there is significant precipitation in the samples. This phenomenon can limit the use of meta-cresol and phenol without the addition of further excipients to remedy the precipitation.

Example 3

Figure 3:
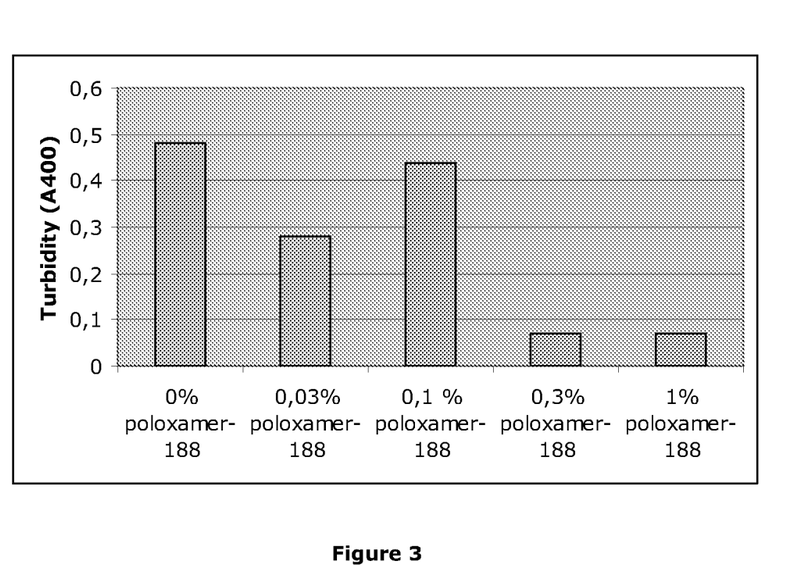
FIG. 3. Turbidity of 15 mg/mL rFVIIa in the presence of 30 mM m-cresol and increasing concentrations of poloxamer-188.

Activated Factor VII was mixed with 30 mM meta-cresol and different concentrations of poloxamer-188 under the following conditions: 15 mg/mL Activated Factor VII, 10 mM histidine, pH 6.0, 20 mM $CaCl_2$, 8% sucrose. Samples with total volumes of 100 µl were dispensed into a quartz microtiter plate (Helima) and the turbidity was assessed by measuring the absorption at 400 nm in a plate reader. It is seen that increasing concentrations of poloxamer-188 gives decreasing turbidity. Thus, inclusion of nonionic surfactants such as poloxamer-188 can in some cases be an advantage.

Example 4

Figure 4:
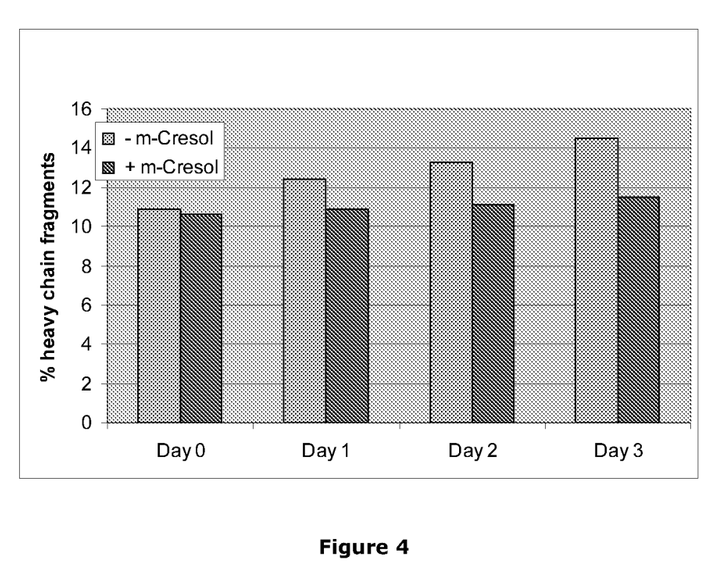
FIG. 4. Formation of heavy-chain fragments in sample containing 5 mg/mL rFVIIa in the presence or absence of 30 mM m-cresol. The sample was held at 37° C. for 3 days.

Solutions with the following composition were prepared: 5 mg/mL Activated Factor VII, 10 mM histidine, pH 6.0, 20 mM $CaCl_2$, 0.1% poloxamer-188, 8% sucrose. Two solutions were prepared: one with 30 mM meta-cresol and one with no meta-cresol. After incubation for three days at 37° C., the amount of heavy chain degradation was measured by reverse-phase HPLC. FIG. 4 shows the result. It is seen that the amount of heavy chain degradation is substantially lower in the presence of meta-cresol, rendering such a formulation advantageous.

Example 5

2 mL of the following solution was freeze-dried: 12 mg/mL activated Factor VII, 0.39 mg/mL NaCl, 5.15 mg/mL $CaCl_2$ ($2H_2O$), 10 mM histidine, 0.5 mg/mL methionine, 0.07% TWEEN® 80, 10 mg/mL sucrose and 25 mg/mL mannitol. The freeze-dried cake was dissolved in 2 mL water and incubated at 5° C. After 2 weeks, the content of heavy chain fragment had increased from about 10% to 19.5%.

Example 6

2 mL of the following solution was freeze-dried: 12 mg/mL activated Factor VII, 0.39 mg/mL NaCl, 5.15 mg/mL $CaCl_2$ ($2H_2O$), 10 mM histidine, 0.5 mg/mL methionine, 0.07% TWEEN® 80, 10 mg/mL sucrose and 25 mg/mL mannitol. The freeze-dried cake was dissolved in 2 mL 1.5% benzyl alcohol, pH was adjusted to 6.0 and the samples were and incubated at 5° C. After 2 weeks, the content of heavy chain fragment had increased from about 10% to 14.5%.

Example 7

5 mL of the following composition were freeze-dried: 1.0 mg/mL activated Factor VII, 2.34 mg/mL NaCl, 1.47 mg/mL calcium chloride, 1.32 mg/mL glycylglycine, 25 mg/mL mannitol, 10 mg/mL sucrose, 0.5 mg/mL methionine, 0.07 mg/mL Tween 80, pH 6.00. The freeze-dried powder was reconstituted in 1.2 mL 0.3% meta-cresol, 10 mM histidine, 0.3% poloxamer-188, pH 6.0. The sample was incubated at 5° C. After 0, 1, 2, 3 and 4 weeks aliquots were withdrawn and frozen. At the end of the experiment, all samples were thawed and analysed for heavy chain fragments and oxidation products. The following table shows the results:

| #Weeks | % Heavy chain fragments | % oxidation products |
|---|---|---|
| 0 | 7.9 | 1.5 |
| 1 | 8.4 | 1.7 |
| 2 | 8.9 | 1.7 |
| 3 | 9.6 | 1.8 |
| 4 | 10.1 | 1.8 |

Both Heavy chain fragmentation and oxidation remain within acceptable limits.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. This invention includes all modifications and equivalents of the subject matter recited in the claims appended hereto as permitted by applicable law.

Preferred Features of the Invention:

A liquid, aqueous pharmaceutical composition comprising at least 10 mg/mL of a Factor VII polypeptide (i);

a buffering agent (ii) suitable for keeping pH in the range of from about 5.0 to about 9.0;

at least one aromatic preservative (iii) in a concentration of at least 0.1 mg/mL; and at least one antioxidant (iv) in a concentration of at least 0.1 mg/mL;

the composition optionally comprising further components, with the proviso that none of such further components are Factor VII polypeptide stabilizing agents selected from
  (a) metal-containing agents, wherein said metal is selected from the group consisting of first transition series metals of oxidation state +II, except zinc; and
  (b) stabilising agent comprising a —C(=N—$Z^1$—O—NH—$Z^2$—$R^2$ motif.

The composition according to the preceding clause, wherein none of said further components are Factor VII polypeptide stabilizing agents.

The composition according to any one of the preceding clauses, wherein the at least one aromatic preservative (iii) is selected from phenol, benzyl alcohol, orto-cresol, meta-cresol, para-cresol, methyl paraben, propyl paraben, benzalkonium chloride, and benzethonium chloride, in particular meta-cresol, phenol and benzyl alcohol.

The composition according to any one of the preceding clauses, wherein the at least one aromatic preservative is included at a concentration of 0.1-20 mg/mL.

The composition according to any one of the preceding clauses, wherein the at least one antioxidant (iv) is selected from L-methionine, D-methionine, methionine analogues, methionine-containing peptides, methionine-homologues, ascorbic acid, cysteine, homocysteine, gluthatione, cystine, and cysstathionine.

The composition according to any one of the preceding clauses, wherein the at least one antioxidant (iv) is present in a concentration of 0.1-5.0 mg/mL.

The composition according to any one of the preceding clauses, wherein the Factor VII polypeptide is human Factor VIIa.

The composition according to any one of the preceding clauses, wherein the Factor VII polypeptide is a Factor VII sequence variant.

The composition according to the preceding clause, wherein the ratio between the activity of the Factor VII polypeptide and the activity of native human Factor VIIa (wild-type FVIIa) is at least 1.25 when tested in the "In Vitro Proteolysis Assay" (Assay 2) as described herein.

The composition according to any one of the preceding clauses, wherein the Factor VII polypeptide is present in a concentration of 10-90 mg/mL.

The composition according to any one of the preceding clauses, which has a pH value in the range of from about 5.0 to about 8.0.

The composition according to any one of the preceding clauses, wherein the buffering agent (ii) comprises at least one component selected from the group consisting of acids and salts of MES, PIPES, ACES, BES, TES, HEPES, TRIS, histidine, imidazole, glycine, glycylglycine, glycinamide, phosphoric acid, acetic acid, lactic acid, glutaric acid, citric acid, tartaric acid, malic acid, maleic acid, and succinic acid.

The composition according to any one of the preceding clauses, wherein the concentration of the buffering agent (ii) is 1-100 mM.

The composition according to any one of the preceding clauses, further comprising a tonicity modifying agent (v).

The composition according to the preceding clause, wherein the tonicity modifying agent (v) is at least one selected from the group consisting of neutral salts, amino acids, peptides of 2-5 amino acid residues, monosaccharides, disaccharides, polysaccharides, and sugar alcohols.

The composition according to any one of the two preceding clauses, wherein at least one tonicity modifying agent (v) is a neutral salt selected from the group consisting of sodium salts, potassium salts, calcium salts, and magnesium salts.

The composition according to any one of the preceding clauses, wherein the tonicity modifying agent (v) is sodium chloride in combination with at least one selected from the group consisting of calcium chloride, calcium acetate, magnesium chloride and magnesium acetate.

The composition according to any one of the preceding clauses, wherein the tonicity modifying agent (v) is present in a concentration of at least 1 mM.

The composition according to any one of the preceding clauses, wherein at least one tonicity modifying agent (v) is an ionic strength modifying agent (v/a).

The composition according to any one of the preceding clauses, which further comprises a non-ionic surfactant (vi).

The composition according to the preceding clause, wherein the non-ionic surfactant (vi) is at least one selected from the group consisting of polysorbates, poloxamers, polyoxyethylene alkyl ethers, ethylene/polypropylene block co-polymers and polyethyleneglycol (PEG).

The composition according to any one of the two preceding clauses, wherein the concentration of the non-ionic surfactant (vi) is 0.005-2% by weight.

The liquid, aqueous pharmaceutical composition according to any one of the preceding clauses, which comprises:
10-90 mg/mL of a Factor VII polypeptide (i);
a buffering agent (ii) suitable for keeping pH in the range of from about 5.0 to about 9.0;
at least one aromatic preservative (iii) in a concentration of 0.1-20 mg/mL; and
at least one antioxidant (iv) in a concentration of 0.1-5.0 mg/mL.

The composition according to any one of the preceding clauses, which is adapted for parenteral administration.

The composition according to the preceding clause, which is adapted for subcutaneous, intramuscular or intravenous injection.

A liquid, aqueous pharmaceutical composition as defined in any one of the preceding clauses for use as a medicament.

Use of a liquid, aqueous pharmaceutical composition as defined in any one of the preceding clauses for the preparation of a medicament for treating a Factor VII-responsive syndrome.

A method for treating a Factor VII-responsive syndrome, the method comprising administering to a subject in need thereof an effective amount of a liquid, aqueous pharmaceutical composition as defined in any one of the preceding clauses.

An air-tight container containing a liquid, aqueous pharmaceutical composition as defined in any one of the preceding clauses, and optionally an inert gas.

A kit for the preparation of the composition as defined in any one of the preceding clauses, said kit comprising:
(a) a first container comprising at least the Factor VII polypeptide (i) in freeze-dried form;
(b) a second container comprising an aqueous reconstitution liquid, said liquid at least comprising the buffering agent (ii) and the at least one aromatic preservative (iii).

The invention claimed is:

1. A liquid aqueous pharmaceutical composition comprising a formulation of:
(i) at least 10 mg/mL of a Factor VII polypeptide;
(ii) a buffering agent suitable for keeping the pH of the composition in a range of from about 5.0 to about 9.0;
(iii) at least one aromatic preservative in a concentration of at least 0.1 mg/mL, wherein the aromatic preservative is selected from the group consisting of phenol, benzyl alcohol, orto-cresol, meta-cresol, para-cresol, methyl paraben, propyl paraben, benzalkonium chloride, and benzethonium chloride;
(iv) at least one antioxidant in a concentration of at least 0.1 mg/mL;
wherein the composition does not contain a Factor VII polypeptide stabilizing agent selected from the group consisting of
(a) a metal-containing agent, wherein the metal is a first transition series metal of oxidation state +II with the exception of zinc; and
(b) a stabilising agent comprising a —C(=N—$Z^1$—$R^1$)—NH—$Z^2$—$R^2$ motif, wherein $Z^1$ and $Z^2$ independently are selected from the group consisting of —O—, —S—, —$NR^H$— and a single bond, $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, and optionally substituted heterocyclyl, or $Z^2$ and $R^2$ are as defined above and —C(=N—$Z^1$—$R^1$ forms part of a heterocyclic ring, or $Z^1$ and $R^1$ are as defined above and —C—NH—$Z^2$—$R^2$ forms part of a heterocyclic ring, or —C(=N—$Z^1$—$R^1$)—NH—$Z^2$—$R^2$ forms a heterocyclic ring wherein —$Z^1$—$R^1$—$R^2$—$Z^2$— is a biradical; and (v) a pharmaceutically acceptable carrier.

2. The composition of claim 1, wherein the composition does not contain an additional Factor VII polypeptide stabilizing agent.

3. The composition of claim 1, wherein the at least one aromatic preservative is included at a concentration of 0.1-20 mg/mL.

4. The composition of claim 1, wherein the (iv) at least one antioxidant is selected from the group consisting of L-methionine, D-methionine, methionine analogues, methionine-containing peptides, methionine-homologues, ascorbic acid, cysteine, homocysteine, gluthatione, cystine, and cysstathionine.

5. The composition of claim 1, wherein the (iv) at least one antioxidant is present in a concentration of 0.1-5.0 mg/mL.

6. The composition of claim 1, further comprising a (v) tonicity modifying agent.

7. The composition of claim 6, wherein the (v) tonicity modifying agent is selected from the group consisting of neutral salts, amino acids, peptides of 2-5 amino acid residues, monosaccharides, disaccharides, polysaccharides, and sugar alcohols.

8. The composition of claim 6, wherein the tonicity modifying agent is a neutral salt selected from the group consisting of sodium salts, potassium salts, calcium salts, and magnesium salts.

9. The composition of claim 6, wherein the (v) tonicity modifying agent is sodium chloride in combination with at least one salt selected from the group consisting of calcium chloride, calcium acetate, magnesium chloride and magnesium acetate.

10. The composition of claim 1, further comprising a (vi) non-ionic surfactant.

11. The composition of claim 10, wherein the (vi) non-ionic surfactant is selected from the group consisting of polysorbates, poloxamers, polyoxyethylene alkyl ethers, ethylene/polypropylene block co-polymers and polyethyleneglycol (PEG).

12. The composition of claim 1, wherein
(i) the Factor VII polypeptide is at a concentration of 10-90 mg/mL;
(ii) the buffering agent is capable of keeping the pH of the composition in the range of from about 5.0 to about 9.0;
(iii) the at least one aromatic preservative is in a concentration of 0.1-20 mg/mL; and
(iv) the at least one antioxidant is in a concentration of 0.1-5.0 mg/mL.

13. The composition of claim 1, wherein the (iii) at least one aromatic preservative is selected from the group consisting of meta-cresol, phenol, and benzyl alcohol.

14. The composition of claim 12, wherein the (iii) at least one aromatic preservative is selected from the group consisting of meta-cresol, phenol, and benzyl alcohol.

15. A method of treating a Factor VII-responsive syndrome, comprising administering to a patient in need thereof a liquid aqueous pharmaceutical composition comprising a formulation of:

(i) at least 10 mg/mL of a Factor VII polypeptide;
(ii) a buffering agent suitable for keeping the pH of the composition in a range of from about 5.0 to about 9.0;
(iii) at least one aromatic preservative in a concentration of at least 0.1 mg/mL, wherein the aromatic preservative is selected from the group consisting of phenol, benzyl alcohol, orto-cresol, meta-cresol, para-cresol, methyl paraben, propyl paraben, benzalkonium chloride, and benzethonium chloride;
(iv) at least one antioxidant in a concentration of at least 0.1 mg/mL;

wherein the composition does not contain a Factor VII polypeptide stabilizing agent selected from the group consisting of
(a) a metal-containing agent, wherein the metal is a first transition series metal of oxidation state +II with the exception of zinc; and
(b) a stabilising agent comprising a —C(=N—$Z^1$—$R^1$)—NH—$Z^2$—$R^2$ motif, wherein $Z^1$ and $Z^2$ independently are selected from the group consisting of —O—, —S—, —$NR^H$— and a single bond, $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, and optionally substituted heterocyclyl, or $Z^2$ and $R^2$ are as defined above and —C=N—$Z^1$—$R^1$ forms part of a heterocyclic ring, or $Z^1$ and $R^1$ are as defined above and —C—NH—$Z^2$—$R^2$ forms part of a heterocyclic ring, or —C(=N—$Z^1$—$R^1$)—NH—$Z^2$—$R^2$ forms a heterocyclic ring wherein —$Z^1$—$R^1$—$R^2$—$Z^2$— is a biradical, wherein the Factor-VII responsive syndrome is selected from the group consisting of haemophilia A, haemophilia B, coagulation Factor XI deficiency, coagulation Factor VII deficiency, thrombocytopenia, von Willebrand's disease, acquisition of clotting Factor inhibitors, intracerebral haemorrhage, and excessive bleeding; and (v) a pharmaceutically acceptable carrier.

16. The method of claim 15, wherein
(i) the Factor VII polypeptide is at a concentration of 10-90 mg/mL;
(ii) the buffering agent is capable of keeping the pH of the composition in the range of from about 5.0 to about 9.0;
(iii) the at least one aromatic preservative is in a concentration of 0.1-20 mg/mL; and
(iv) the at least one antioxidant is in a concentration of 0.1-5.0 mg/mL.

17. The method of claim 15, wherein the Factor-VII responsive syndrome is selected from the group consisting of haemophilia A, haemophilia B, coagulation Factor XI deficiency, and coagulation Factor VII deficiency.

18. The method of claim 17, wherein the Factor-VII responsive syndrome is haemophilia A.

19. The method of claim 17, wherein the Factor-VII responsive syndrome is haemophilia B.

20. The method of claim 17, wherein the Factor-VII responsive syndrome is coagulation Factor XI deficiency.

21. The method of claim 17, wherein the Factor-VII responsive syndrome is coagulation Factor VII deficiency.

* * * * *